(12) United States Patent
Warner et al.

(10) Patent No.: US 9,727,693 B2
(45) Date of Patent: Aug. 8, 2017

(54) AUTOMATED TRACKING OF A MEDICAL PROCEDURE USING MACROS

(71) Applicant: General Electric Company, Schenectady, NY (US)

(72) Inventors: Adrian F. Warner, Wauwatosa, WI (US); Daniel Richard Schneidewend, Wauwatosa, WI (US); Linda Marie Helvick, Wauwatosa, WI (US); Venkat Krishnan, Plainsboro, NJ (US); Angela Orentas, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/803,411

(22) Filed: Jul. 20, 2015

(65) Prior Publication Data

US 2017/0024522 A1    Jan. 26, 2017

(51) Int. Cl.
| | |
|---|---|
| G06K 7/10 | (2006.01) |
| G06F 19/00 | (2011.01) |
| A61B 19/00 | (2006.01) |
| A61B 5/0402 | (2006.01) |
| A61B 5/00 | (2006.01) |
| A61B 90/00 | (2016.01) |

(52) U.S. Cl.
CPC .......... *G06F 19/323* (2013.01); *A61B 5/7495* (2013.01); *A61B 19/54* (2013.01); *G06F 19/327* (2013.01); *A61B 5/0402* (2013.01); *A61B 5/742* (2013.01); *A61B 5/7475* (2013.01); *A61B 90/00* (2016.02); *A61B 2019/5483* (2013.01)

(58) Field of Classification Search
CPC ....... A61B 90/96; A61B 5/0402; A61B 5/742; A61B 19/54; A61B 2019/5483; A61B 90/00; A61B 5/7475; A61B 5/7495; G06F 19/3481; G06F 19/327; G06F 19/323
USPC .................................................. 235/441, 454
See application file for complete search history.

(56) References Cited

U.S. PATENT DOCUMENTS

| | | | |
|---|---|---|---|
| 6,571,294 B2 | 5/2003 | Simmon et al. | |
| 6,571,297 B1 | 5/2003 | Cline et al. | |
| 8,523,075 B2 | 9/2013 | van der Merwe | |
| 8,928,746 B1* | 1/2015 | Stevrin | G02B 23/2461 348/68 |
| 2001/0016681 A1* | 8/2001 | Pratt | A01K 5/02 600/300 |
| 2002/0195488 A1* | 12/2002 | Walsh | A61N 5/1048 235/380 |
| 2003/0074228 A1* | 4/2003 | Walsh | A61N 5/1048 705/3 |
| 2003/0233276 A1* | 12/2003 | Pearlman | G06Q 20/3274 705/14.23 |
| 2004/0243444 A1* | 12/2004 | Steusloff | G06F 3/002 705/2 |

(Continued)

FOREIGN PATENT DOCUMENTS

WO    2014/044139 A1    3/2014

*Primary Examiner* — Claude J Brown
(74) *Attorney, Agent, or Firm* — Andrus Intellectual Property Law LLP

(57) ABSTRACT

A system for tracking a medical procedure includes a set of macros, a scanning device, and a control unit. Each macro in the set of macros is associated with instructions that execute a tracking step of a medical procedure. The scanning device is controlled by a user during the medical procedure to select a macro from the set of macros. The control unit executes the instructions associated with the selected macro to track the medical procedure.

20 Claims, 5 Drawing Sheets

(56) References Cited

U.S. PATENT DOCUMENTS

| | | | | |
|---|---|---|---|---|
| 2005/0008261 A1* | 1/2005 | Wolff | G06F 17/30817 | 382/305 |
| 2005/0125301 A1* | 6/2005 | Muni | G06Q 30/06 | 705/23 |
| 2005/0128184 A1* | 6/2005 | McGreevy | A61B 18/1206 | 345/156 |
| 2006/0000910 A1* | 1/2006 | Chong | H04W 28/18 | 235/462.15 |
| 2006/0138211 A1* | 6/2006 | Lubow | G06K 17/00 | 235/375 |
| 2008/0109260 A1* | 5/2008 | Roof | G06F 19/3406 | 705/3 |
| 2009/0317002 A1* | 12/2009 | Dein | A61B 19/0256 | 382/224 |
| 2010/0231509 A1* | 9/2010 | Boillot | G06F 3/011 | 345/156 |
| 2011/0024491 A1* | 2/2011 | Jamali | A61B 90/96 | 235/375 |
| 2011/0180600 A1* | 7/2011 | Wang | G06Q 20/208 | 235/383 |
| 2012/0086958 A1* | 4/2012 | Srnka | G06F 3/1208 | 358/1.6 |
| 2012/0284051 A1* | 11/2012 | Standaert | G06Q 10/10 | 705/3 |
| 2013/0098983 A1* | 4/2013 | Neff | G06K 17/0025 | 235/375 |
| 2013/0285947 A1* | 10/2013 | Hunter | G09G 5/003 | 345/173 |
| 2014/0071023 A1* | 3/2014 | Chu | G06F 1/1626 | 345/3.1 |
| 2014/0263660 A1* | 9/2014 | Jiang | G06K 19/06112 | 235/491 |
| 2016/0000537 A1* | 1/2016 | Schneider | A61C 9/0053 | 703/1 |
| 2016/0041957 A1* | 2/2016 | Finsterwald | G06F 3/0484 | 715/202 |
| 2016/0157803 A1* | 6/2016 | Keller | A61B 6/504 | 600/427 |

\* cited by examiner

AUTOMATED TRACKING OF A MEDICAL PROCEDURE USING MACROS

BACKGROUND

Medical procedures generally follow a prescribed set of steps, and each step is accompanied by documentation requirements. Thus, medical providers administering procedures must follow those steps and, at the same time, meet the documentation requirements. Existing systems and methods for tracking medical procedures require entry of tracking data into a computer system via a standard mouse and keyboard. This requires a patient care provider to multitask in order to document the medical procedure and operate patient care equipment used to execute the procedure. This can be difficult and demanding on clinicians, as their attention must be drawn to several things simultaneously, and can lead to mistakes.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one embodiment, a system for tracking a medical procedure includes a set of macros, a scanning device, and a control unit. Each macro in the set of macros is associated with instructions that automatically execute a tracking step of a medical procedure. The scanning device is controlled by a user during the medical procedure to select a macro from the set of macros. The control unit executes the instructions associated with the selected macro to track the medical procedure.

One embodiment of a method of tracking a medical procedure includes generating a set of macros, wherein each macro in the set of macros is associated with instructions that automatically execute a tracking step of the medical procedure. The method further includes displaying at least a portion of the set of macros, and receiving a selected macro from a scanning device. The instructions associated with the selected macro is then retrieved and executed.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

Through their experimentation and research in the relevant field, the present inventors have recognized that a method and system is needed for tracking a medical procedure that does not require significant or time consuming input from a user, such as a clinician or other medical care provider. Moreover, the present inventors have recognized that it would be especially beneficial to have a tracking system wherein certain routine portions of a medical procedure, and/or the tracking thereof, could be automated. Thus, the amount of input needed from the user in order to control and document the flow of a medical procedure is minimized, allowing the user to focus on performance of the medical procedure. Additionally, the inventors have recognized that such a tracking system with automation may be used to provide instruction and/or guidance to a user regarding documentation or procedural steps that must be executed. Thereby, the tracking system and method can streamline work flow and ensure that all required documentation and procedural steps are completed and accurately documented.

Figure 1:
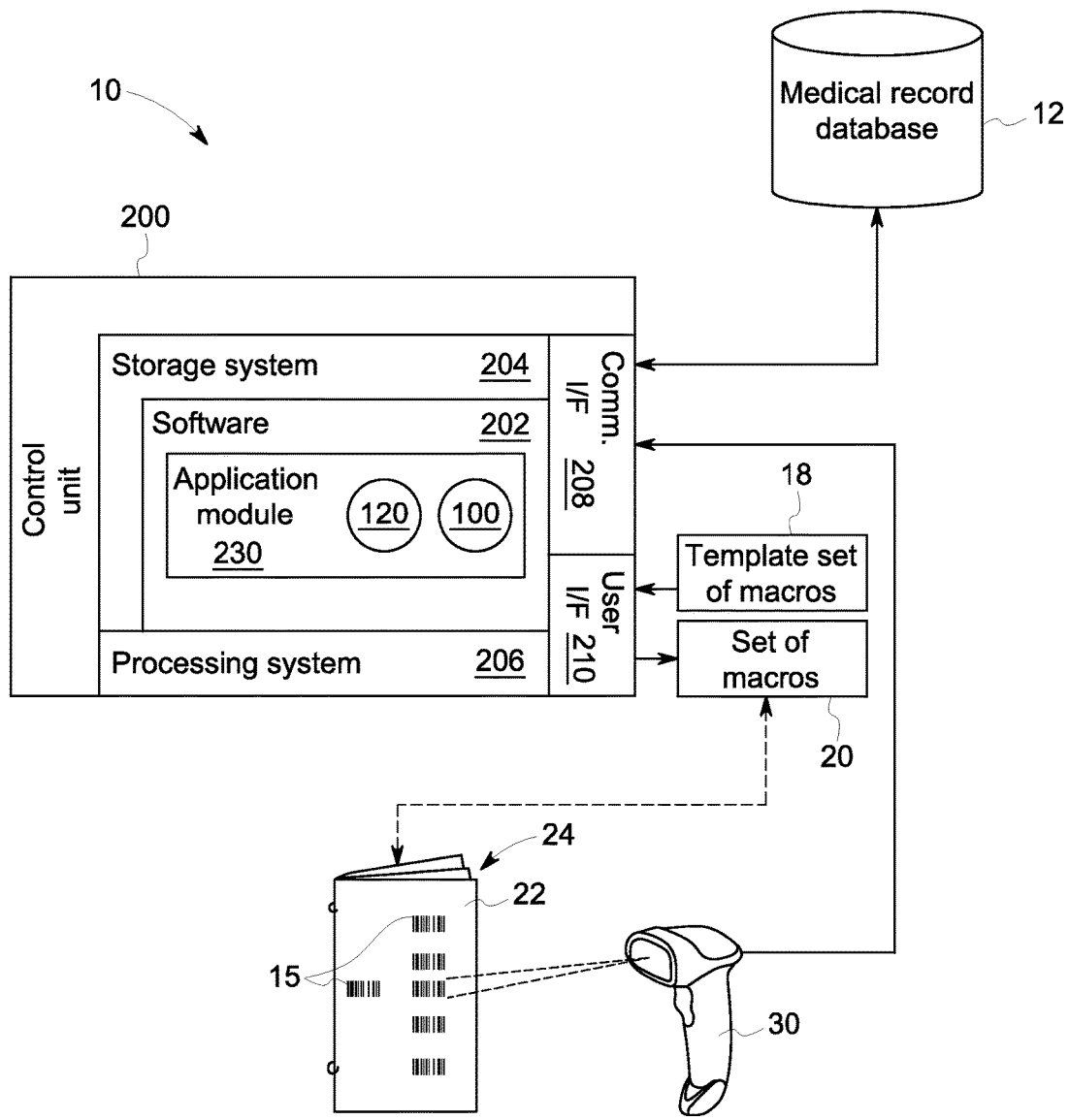
FIG. 1 is a system diagram depicting an exemplary system for tracking a medical procedure.

FIG. 1 depicts one embodiment of a system 10 for tracking a medical procedure. The system 10 includes a control unit 200 that executes certain steps and processes as described herein. The control unit 200 receives input from a user-controlled scanning device 30, which communicates a selected macro 15 to the control unit 200. The control unit 200 associates certain instructions with that selected macro 15. For example, the control unit 200 may have a database wherein each macro 15 in a set of macros 20 is associated with instructions that each automatically execute a particular documentation or other routine step in a medical procedure. As will be known to one of skill in the art, a macro is a pattern, or input sequence, that expands automatically into a set of instructions to perform a particular task. Thus, upon receipt of the selected macro 15, the control unit 200 automatically executes the associated instructions.

The set of macros 20 is generated by the control unit 200 and is output in some manner that enables the user 8 to select one of the macros 15 in the set of macros 20. In exemplary embodiments, the set of macros 20 is a set of unique barcodes, colors, logos, or other visual indicators that each represent, or are associated with, a set of instructions that execute tasks related to tracking a medical procedure. Thereby, the macros 15 trigger specified events and/or actions in a medical case flow. For example, selectable macros 15 might trigger an instruction to document patient information, log a certain measure, capture an event, or append certain information to a record of a medical procedure. Accordingly, the macros 15 may direct communication between the control unit 200 and certain patient monitors or other medical devices, and/or may even control the operation of those devices.

Figure 2:
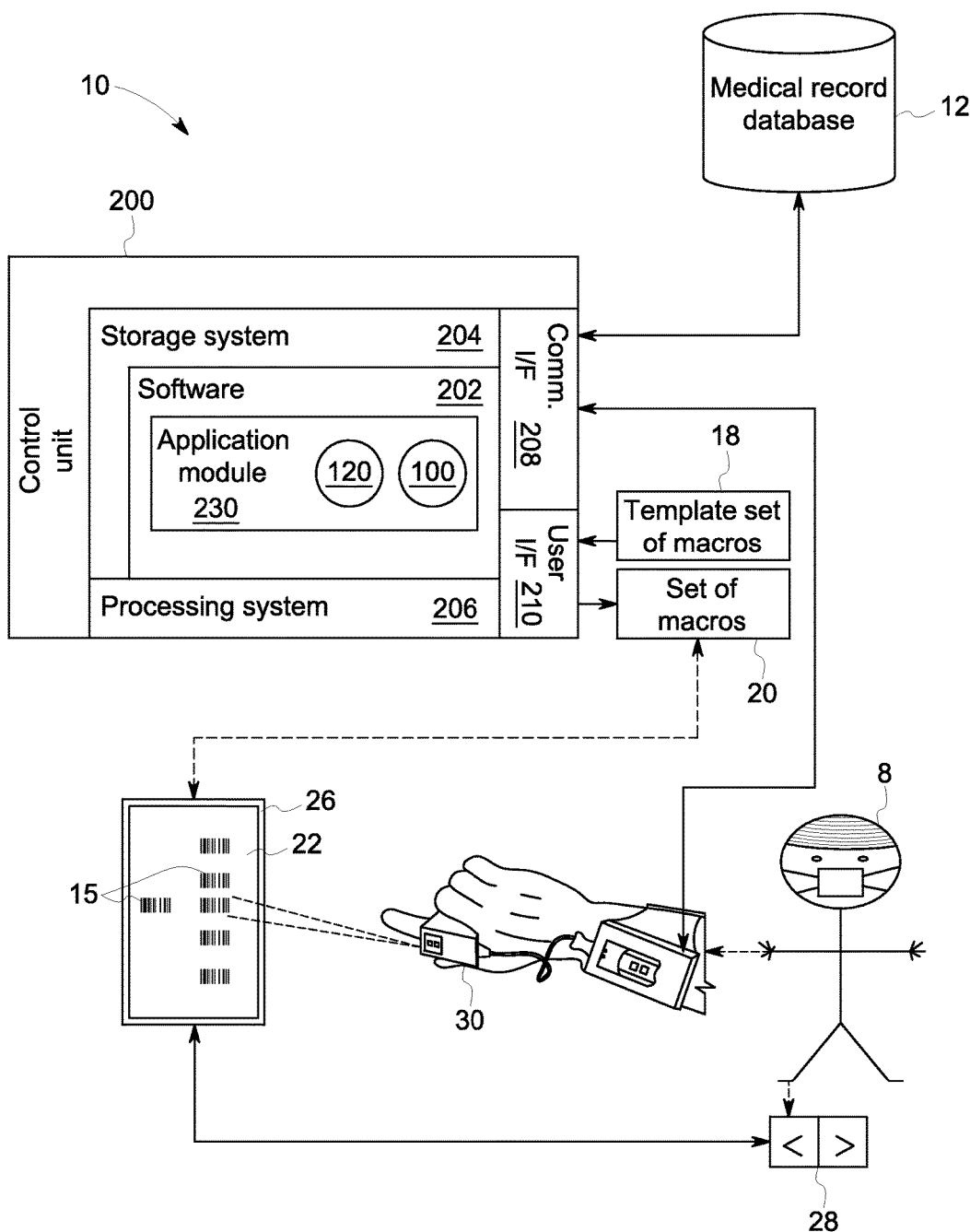
FIG. 2 is a system diagram depicting another embodiment of a system for tracking a medical procedure

The scanning device 30 scans a selected macro 15 in a set of macros 20, and then communicates the selected macro to the control unit 200. In the exemplary embodiment of FIG. 1, the scanning device 30 is a scanner gun, which may be a charge-coupled device (CCD) reader, a laser scanner, an image scanner, or other similar device capable of scanning a pattern of some sort. In the embodiment of FIG. 2, the scanning device 30 is a ring scanner. Ring scanner scanning devices are known in the art, and are scanning devices that can be worn by a user and allow a user to use their hands to perform other tasks while still operating the scanning device 30. For example, the ring scanner scanning device 30 may be worn on a user's finger, such as their index finger, and may contain buttons that can be pressed by the neighboring fingers, such as the thumb or middle finger, to operate the ring scanner scanning device 30 to select macros 15 displayed on the display device 26.

The scanning device 30—whether a ring scanner, scanner gun, or another scanning device—may communicate a selected macro 15 to the control unit 200 by wireless or wired means. Thus, the scanning device 30 may be plugged into the communication interface 208 of the control unit 200, or it may communicate with the communication interface 208 by wireless protocol, such as Bluetooth, Wi-Fi, wireless medical telemetry service (WMTS), or the like. Once a macro 15 is communicated from the scanning device 30 to the control unit 200, the tracking module 120 performs method steps to track the medical procedure, including retrieving the instruction associated with the selected macro 15 and directing execution of that instruction. As described above, the instructions associated with each macro 15 execute actions related to tracking the medical procedure.

In and embodiment that includes a display device, such as the embodiment of FIG. 2, the tracking module 120 may further operate the display device 26 to provide receipt confirmation of the selected macro 15 and/or execution of the associated instructions. For example, the tracking module 120 may operate the display device 26 to display an updated record of the medical procedure, or to display the result of the executed tracking step instructions—e.g. displaying "Patient arrived at 8:05 am" to confirm receipt of the macro 15 for the patient arrives step 47. Alternatively or additionally, the tracking module 120 may operate the display device 26 to generate guidance to the user based on the selected macro 15 and the associated instructions. For example, the display device 26 may display the next steps that should occur in the procedure and/or additional information required to complete a particular phase of the medical procedure. For example, after scanning the macro 15 for the patient arrives step 47, the display device 26 may display a guidance notice to the user to document the patient's allergies. Alternatively or additionally, the tracking module 120 may adjust the display device 26 to display a new or revised sheet 22 of macros 15 once a particular macro 15 has been selected, and/or once a step in a procedure has been completed.

A generation tool 100 allows a user to generate a set of macros 20 for a medical procedure. The set of macros 20 encompasses some or all of the steps that may need to be automated during the procedure, and particularly the documentation and/or patient monitoring steps. In one embodiment, the generation tool 100 may utilize a template set of macros 18. An appropriate template set of macros 18 may be selected by a user from a database of templates, or may be automatically selected by the generation tool 100. For example, several template sets of macros 18 may be generated for common procedures, and may be modifiable by a user to tailor the template to the particular work flow or exact procedure that will be executed by the user. In one exemplary embodiment, the template set of macros 18 may be a style sheet or other editable document containing macros 15 for common steps executed in that procedure. In another embodiment, the generation tool 100 may be a software module that provides a flow chart tool allowing a user to choose macros 15 for each phase of a procedure—i.e., the actions that they want to be able to automate at each phase of the medical procedure. The generation tool 100 may then assemble the set of macros 20 for that medical procedure to include the macros 15 chosen by the user.

The set of macros 20 is then displayed to the user in a way that the user may select macros 15 to track a medical procedure. The set of macros 20 may be displayed to a user in any number of ways, including printing the macros 15 on a physical sheet or displaying them on a digital display. In the exemplary embodiment of FIG. 1, the set of macros 20 is divided into sheets 22 of macros 15, the sheets 22 are printed and assembled into a book 24. For example, the printed sheets 22 in the depicted embodiment may be printed on paper and laminated so that they are durable enough for a medical environment and can be cleaned. In the embodiment of FIG. 2, the set of macros 20 is divided into sheets 22, and the sheets 22 of macros 15 are digitally displayed on a display device 26. For example, the display device 26 may be a tablet or other screen visible by a user to select a macro 15 via the scanning device 30. The scanning device 30 is used to scan a macro 15 from the displayed sheet 22, whether from the display device 26 or the book 24, in order to select that macro and execute the associated macro in order to track the medical procedure.

Each sheet 22 contains several macros 15 that are organized, for example, in relation to a particular action or step in the medical procedure. Thus, each sheet 22 contains a set of related macros 15 that the user may choose between for tracking a particular event or aspect in a procedure. Examples of a set of related macros 15 would be macros 15 that automate the documentation of potential allergies that the patient could have, or macros 15 that automate the capturing of vitals from monitoring devices.

The display 26 may be controlled by a user in order to display different macros 15 or sheets 22 of macros 15. For example, the display 26 may be a touch screen device and the user may swipe or press a portion of the screen in order to flip to various sheets 22 of macros 15. In other embodiments, the display 26 may be associated with a remote display control 28 that may allow a user to change the displayed sheet 22. Such an embodiment would allow the user 8 to change sheets 22 of macros 15 displayed on the display device 26 from a distance and without having to touch the display device 26. In sterile embodiments where a user 8 might be scrubbed in, or in other environments where the user's hands might be occupied, a remote display control 28 would allow the user to operate the display device 26 without having to touch it. For example, the remote display control 28 may be a foot pedal operated by the user to scroll through sheets 22. For example, the foot pedal embodiment of the remote display control 28 may have two pedals, one for scrolling forward and the other for scrolling backwards. In still other embodiments, the remote display control 28 could be a handheld remote control, a gesture remote control, or a voice-controlled remote control. In another exemplary embodiment, the remote display control 28 may integrated into the ring scanner embodiment of the scanning device 30.

Figure 3:
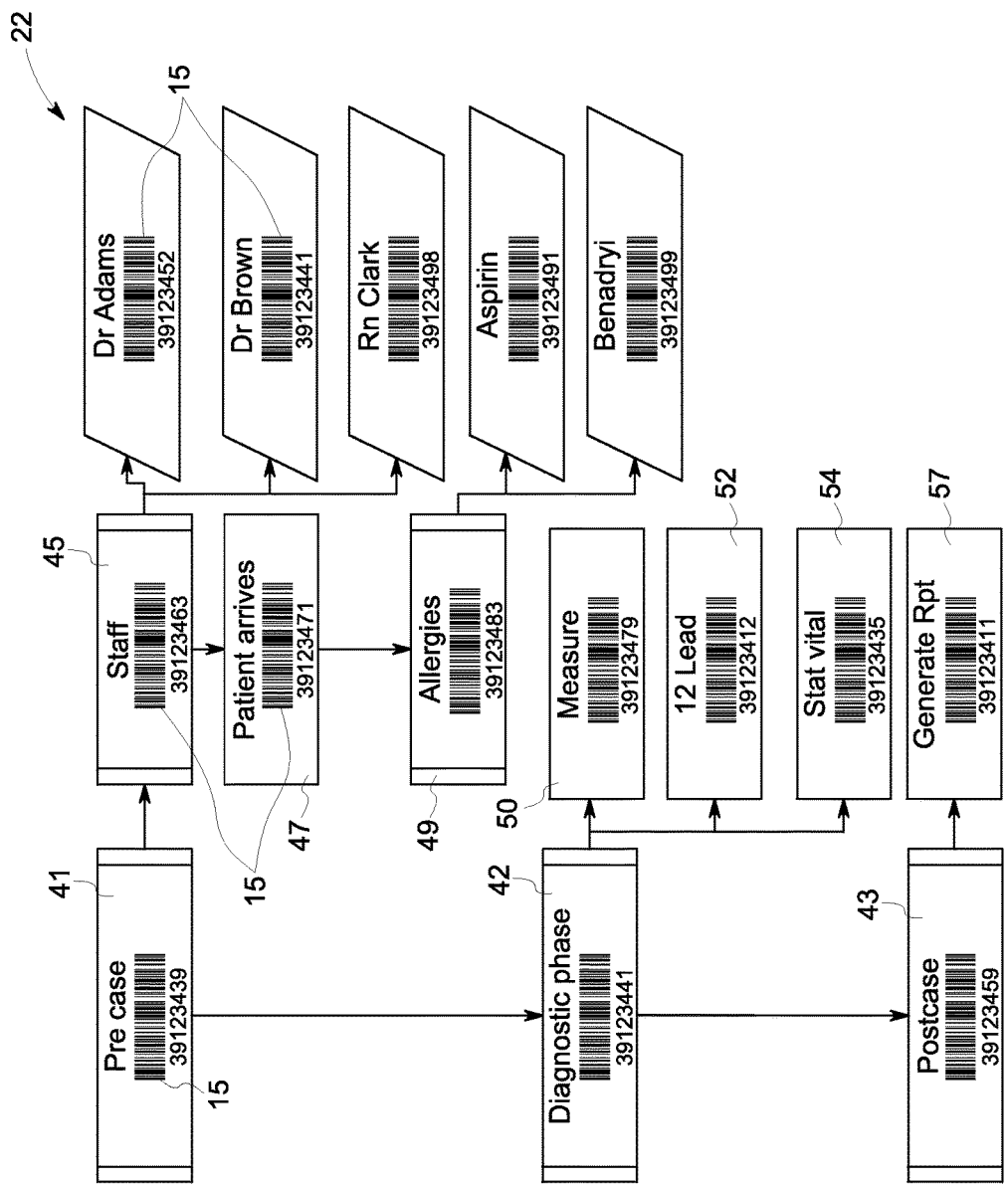
FIG. 3 depicts an exemplary barcode sheet.
Figure 4:
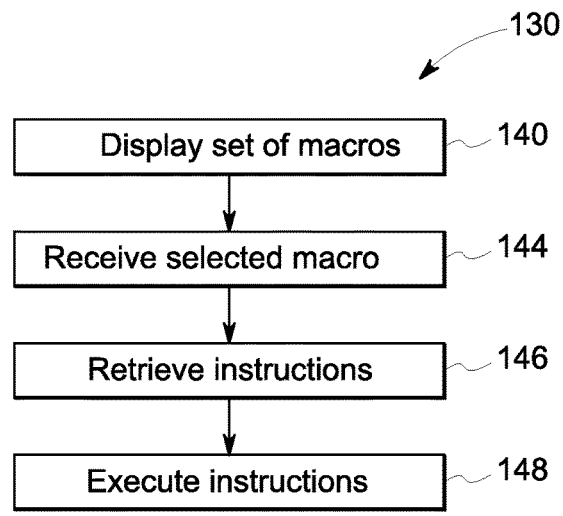
FIG. 4 is a flow chart depicting one embodiment of a method for tracking a medical procedure.
Figure 5:
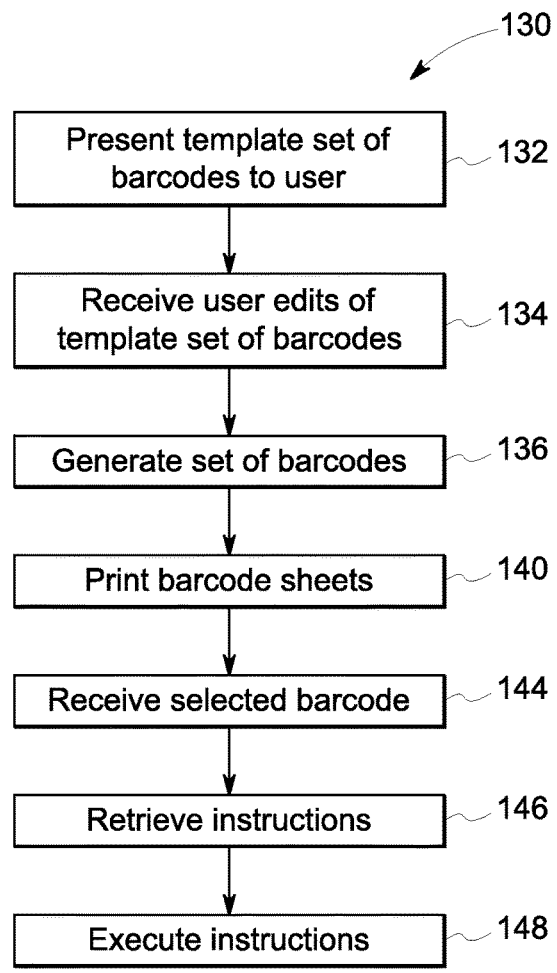
FIG. 5 is a flowchart depicting another embodiment of a method for tracking a medical procedure.
Figure 6:
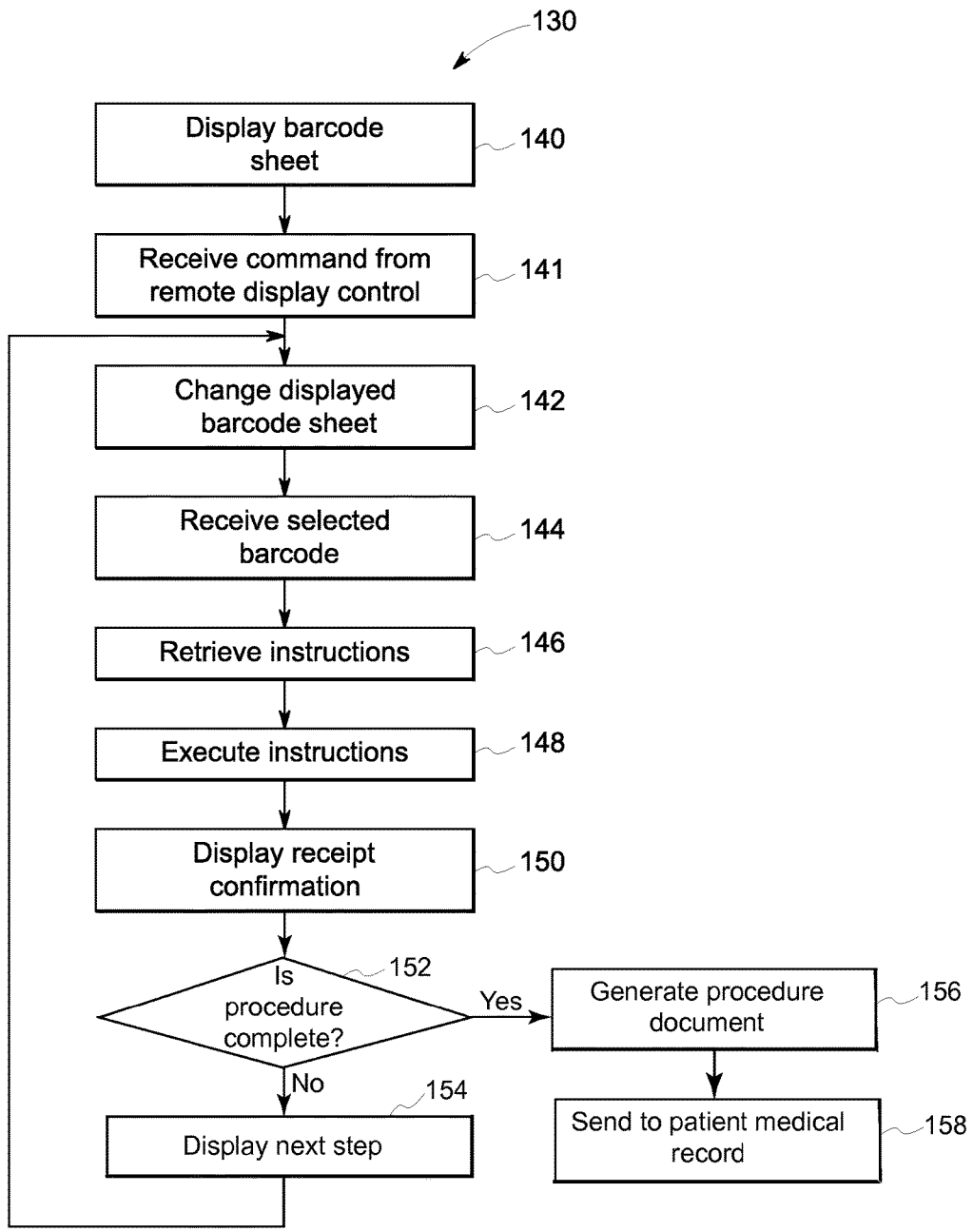
FIG. 6 is another embodiment of a method for tracking a medical procedure.

FIG. 3 presents an exemplary embodiment of a sheet 22 of macros 15. In the example of FIG. 3, the macros 15 are barcodes. The barcodes 15 are organized according to a flow chart that represents steps, or phases, of a medical procedure. In the exemplary sheet 22, barcodes for three phases are provided, a precase phase 41, a diagnostic phase 42, and a postcase phase 43. For each such phase, barcode macros 15 are provided for various steps that may be executed and/or documented. For example, a user may execute the staff documentation step 45 that automatically documents the presence of the staff members, Dr. Adams, Dr. Brown, and Rn Clark as the barcode macros 15 of those individuals is scanned. Likewise, the user may document when the patient arrives by scanning the barcode 15 of the patient arrives step 47. In the same manner, the user may document the allergies of a patient at step 49 by scanning the macros 15 associated with any allergies that the patient might have.

Thus, the user may progress through several different sheets 22 as they progress through a medical procedure, scanning macros 15 at each phase and step to track and create a record of the procedure. Further, the user can direct and automate the operation and/or interaction with certain patient monitoring devices or other patient care devices using the macros 15. In the exemplary sheet 22 shown in FIG. 3, the user may automate documentation of the diagnostic phase 42 by selecting the macro 15 for the measure step 50 to measure a particular physiological signal. Likewise, the user may scan the macro 15 for the 12 lead step 52 to instruct an ECG device to automatically capture an ECG recording, e.g., for a particular length of time or until the detection of a particular event. Likewise, the user may instruct automatic documentation of the patient's vitals by scanning the macro 15 for the stat vital step 54.

The sheets 22 of indicators 15 may be organized in any way that allows for progression through the sheets 22 in order to track the medical procedure. In one example where the sheet 22 is displayed on a digital display device 26, once a phase or step is completed, the macros 15 related to the completed step or phase may disappear from the sheet 22 and may be replaced by other phases and/or steps that remain to be executed. Alternatively, the sheet 22 may remain as is on the display device 26 until either all of the phases and steps are completed, or until the user 8 provides an instruction to change the sheet 22. Likewise, once all of the phases of a case are completed, e.g., when a particular macro 15 is scanned (such as a "patient leaves" macro) or when at least one macro 15 scanned at each phase, the system may automatically generate a report and/or store the tracking information of the medical procedure in the patient's medical record. In another embodiment, the user may select a macro 15 that completes the postcase phase 43 and executes the generate report step 57.

Returning to FIGS. 1 and 2, the system diagram illustrates an exemplary embodiment of the control unit 200 that implements the generation tool 100 that generates the set of macros 20, and the tracking module 120 that retrieves and executes the instructions associated with a selected macro 15 in order to track the medical procedure. The control unit 200 is generally a computing system that includes a processing system 206, storage system 204, software 202, communication interface 208, and user interface 210. The processing system 206 holds and executes software 202 from the storage system 204, including a software application module 230. The software application module 230 includes the generation tool 100 and the tracking module 120, which may be individually executed. When executed by the control unit 200, software module 230 directs the processing system 206 to operate as described to execute the methods described herein, including execution of the generation tool 100 and/or the tracking module 120. The software application module 230 also directs the processing system 206 to store information in order to track the medical procedure and create a record thereof as described herein. Alternatively or additionally, the software application module 230 may also direct the processing system 206 to store information in the medical record database 12, which may be separate from the storage system 204 associated directly with the control unit 200.

Although the control unit 200 as depicted in FIGS. 1 and 2 includes only a few exemplary software modules, it should be understood that any number of software modules can be included, and that the operations described with respect to the two representative modules could be provided by a single module or by any number of additional modules. Similarly, while the description as provided herein refers to a control unit 200 and a processing system 206, it is to be recognized that implementation of such systems can be performed using one or more control units, having one or more processors, which may be communicatively connected, and that such implementations are considered to be within the scope of the description.

The processing system 206 can comprise a microprocessor and other circuitry that retrieves and executes software 202 from storage system 204. Processing system 206 can be implemented within a single processing device, or can be distributed across multiple processing devices or sub-systems that cooperate in executing program instructions. Exemplary processing systems 206 include general purpose central processing units, application specific processors, logic devices, as well as any other type of processing device, combinations of processing devices, or variations thereof.

The storage system 204 can comprise any storage media readable by processing system 206 and capable of storing software 202. The storage system 204 can include volatile and/or non-volatile, removable and/or non-removable media, implemented in any method or technology for storage of information, such as computer-readable instructions, data structures, program modules, or other data. Storage system 204 can be implemented as a single storage device, or may be implemented across multiple storage devices or storage sub-systems. Storage system 204 can further include additional elements, such as a controller capable of communicating with the processing system 206.

Examples of storage media include random access memory, read-only memory, magnetic discs, optical discs, flash memory, virtual memory, a non-virtual memory, a magnetic storage device, or any other medium which can be used to store the desired information and that may be accessed by an instruction execution system, as well as any combination or variation thereof, or any other type of storage media. In some implementations, the storage media can be a non-transitory storage media. In some implementations, at least a portion of the storage media may be transitory.

The user interface 210 may include a mouse, a keyboard, a voice input device, a touch input device, a motion or gesture input device, or the like and associated processing elements capable of receiving user input from a user. Output devices such as a video display or graphical display can display an interface for the user and may further be included with embodiments of the control unit 200 as described herein. Speakers, printers, haptic devices, and other types of output devices may also be included in the user interface 210. In one example, the user interface 210 includes a touchscreen device, or alternatively a computer display, keyboard, and mouse, that allows a user to provide input to generate the set of macros 20. For example, the user may select a template set of macros 18 near the user interface 210, and edit that template set of macros 18 to create the set of macros 20.

One embodiment of a method 130 of tracking a medical procedure includes displaying a set of macros 20, or a subset thereof (such as a sheet 22 of macros), at step 140. At step 144, a selected macro is received. An instruction associated with that selected macro is retrieved at step 146. Then, at step 148, the instruction is executed to track the medical procedure.

In another embodiment, a method 130 of tracking a medical procedure begins by presenting a template set of barcodes to a user at step 132. At step 134, edits to the template set of barcodes are received. Based on the edits, a set of barcodes for a medical procedure is generated at step 136. Barcode sheets are printed at step 140. At step 144, the selected barcode is received, for example, from scanning device 30. Instructions associated with the selected barcode are retrieved at step 146, and the instructions are executed at step 148.

In another embodiment, a method 130 of tracking a medical procedure includes displaying a barcode sheet at step 140, for example on a digital display device 26. At step 141, a command is received from a remote display control. In response to the command, the displayed barcode sheet is changed at step 142. At step 144, a selected barcode is received, and associated instructions are retrieved at step 146. The instructions are then executed at step 148. Receipt confirmation of the selected barcode and associated instructions is displayed at 150, for example on the digital display device 26. At step 152, it is determined whether the procedure is complete, or whether more steps remain to be executed. If the procedure is not complete, then a next step indication is then displayed to the user at step 154, such as to give the user guidance on what actions or documentation should be selected next. The tracking module 120 then returns to step 142 where a change is made to the displayed barcode sheet. For example, the barcodes 15 related to the tracking step that was just executed may be removed from the barcode sheet 22. If it is determined at step 152 that the procedure is complete, then a procedure document, or record, may be generated at step 156. At step 158, that document may be sent to the patient's medical record, which may be in the medical record database 12.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system for tracking a medical procedure, the system comprising:
    a set of macros, wherein each macro in the set of macros is associated with instructions to automatically execute a tracking step of a medical procedure;
    a scanning device;
    a control unit;
    wherein the scanning device is controlled by a user during the medical procedure to select a macro from the set of macros, and wherein the control unit executes the instructions associated with the selected macro to track the medical procedure; and
    a display device that displays at least a portion of the set of macros, wherein the display device is separate from the scanning device such that the macros are scannable by the scanning device.

2. The system of claim 1, further including a generation tool that allows the user to generate the set of macros prior to the medical procedure.

3. The system of claim 2, wherein the generation tool comprises at least one template set of macros that is editable by the user.

4. The system of claim 3, wherein the generation tool further comprises at least one style sheet.

5. The system of claim 1, wherein the macro is a barcode, and the set of macros is a set of barcodes arranged into at least one barcode sheet.

6. The system of claim 1, wherein the display device is controlled by the user with a remote display control.

7. The system of claim 1, wherein the remote display control is a foot pedal that allows the user to control which macros are displayed on the display device.

8. The system of claim 7, wherein the scanning device is operable by the user from within a sterile field to scan the macros on the display device to track the medical procedure, wherein the display device is outside of the sterile field.

9. The system of claim 1, wherein the set of macros is a set of barcodes.

10. A method of tracking a medical procedure, the method comprising:
    generating a set of macros, wherein each macro in the set of macros is associated with instructions that automatically execute a tracking step of a medical procedure;
    displaying at least a portion of the set of macros, including displaying a first sheet of macros on a display device, wherein each of the macros in the sheet of macros is scannable with a scanning device to execute the tracking step of the medical procedure;
    receiving a selected macro from the scanning device;
    retrieving the instructions associated with the selected macro; and
    executing the instructions.

11. The method of claim 10, further including updating the display device upon execution of the instructions.

12. The method of claim 11, wherein updating the display device includes displaying a receipt confirmation.

13. The method of claim 11, wherein updating the display device includes displaying a second sheet of macros.

14. The method of claim 11, wherein updating the display device includes displaying a next step.

15. The method of claim 10, wherein the macro is a barcode, and wherein displaying the set of barcodes includes generating barcode sheets, each barcode sheet containing a portion of the set of barcodes.

16. The method of claim 10, further including generating the set of macros with input from a user.

17. The method of claim 16, further including presenting a template set of macros to a user and receiving edits to the template set of macros from the user.

18. The method of claim 10, wherein the scanning device is operated by a user from within a sterile field to scan the macros on the display device outside the sterile field; and
    further including receiving input from a remote display control; and
    changing the portion of the set of macros displayed on the display device in response to the input.

19. The method of claim 18, wherein the scanning device is operated by a user from within a sterile field to scan the macros on the display device outside the sterile field; and
    wherein the remote display control is a foot pedal.

20. A method of tracking a medical procedure, the method comprising:
    generating a set of macros, wherein each macro in the set of macros is associated with instructions that automatically execute a tracking step of a medical procedure;
    displaying a first sheet of macros on a display device, wherein each of the macros in the sheet of macros is scannable with a scanning device to execute the tracking step of the medical procedure;
    receiving a user input to the scanning device to scan one of the set of macros on the display device, wherein the scanning device is operated by a user from within a sterile field when the display device is outside the sterile field;

receiving a selected macro from the scanning device, wherein the selected macro is the scanned one of the set of macros;

retrieving the instructions associated with the selected macro;

executing the instructions;

receiving input from a remote display control to change the sheet of macros displayed on the display device, wherein the remote display control is operated by a user from within the sterile field to control the display device outside of the sterile field; and displaying a second sheet of macros on the display device displayed in response to the input.

\* \* \* \* \*